US008901490B1

(12) United States Patent
Chen et al.

(10) Patent No.: US 8,901,490 B1
(45) Date of Patent: Dec. 2, 2014

(54) ION MANIPULATION DEVICE WITH ELECTRICAL BREAKDOWN PROTECTION

(71) Applicants: Tsung-Chi Chen, Richland, WA (US); Keqi Tang, Richland, WA (US); Yehia M. Ibrahim, Richland, WA (US); Richard D. Smith, Richland, WA (US); Gordon A. Anderson, Benton City, WA (US); Erin M. Baker, West Richland, WA (US)

(72) Inventors: Tsung-Chi Chen, Richland, WA (US); Keqi Tang, Richland, WA (US); Yehia M. Ibrahim, Richland, WA (US); Richard D. Smith, Richland, WA (US); Gordon A. Anderson, Benton City, WA (US); Erin M. Baker, West Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 14/292,448

(22) Filed: May 30, 2014

Related U.S. Application Data

(63) Continuation of application No. 14/146,922, filed on Jan. 3, 2014.

(60) Provisional application No. 61/809,660, filed on Apr. 8, 2013.

(51) Int. Cl.
*H01J 49/42* (2006.01)
(52) U.S. Cl.
USPC .......................................... 250/290; 250/292
(58) Field of Classification Search
USPC ................................................. 250/290, 292
See application file for complete search history.

(56) References Cited

U.S. PATENT DOCUMENTS

| 5,572,035 | A | 11/1996 | Franzen |
| 6,107,628 | A | 8/2000 | Smith et al. |
| 6,960,760 | B2 | 11/2005 | Bateman et al. |
| 7,365,317 | B2 | 4/2008 | Whitehouse et al. |
| 7,391,021 | B2 | 6/2008 | Stoermer et al. |
| 7,786,435 | B2 * | 8/2010 | Whitehouse et al. ......... 250/292 |

(Continued)

FOREIGN PATENT DOCUMENTS

| EP | 1566828 A2 | 2/2005 |
| EP | 1825495 B1 | 11/2011 |

OTHER PUBLICATIONS

International Search Report/Written Opinion for International Application No. PCT/US14/11291, International Filing Date Jan. 13, 2014, Date of Mailing Jun. 6, 2014.

(Continued)

*Primary Examiner* — Kiet T Nguyen
(74) *Attorney, Agent, or Firm* — A. J. Gokcek

(57) ABSTRACT

An ion manipulation method and device is disclosed. The device includes a pair of substantially parallel surfaces. An array of inner electrodes is contained within, and extends substantially along the length of, each parallel surface. The device includes a first outer array of electrodes and a second outer array of electrodes. Each outer array of electrodes is positioned on either side of the inner electrodes, and is contained within and extends substantially along the length of each parallel surface. A DC voltage is applied to the first and second outer array of electrodes. A RF voltage, with a superimposed electric field, is applied to the inner electrodes by applying the DC voltages to each electrode. Ions either move between the parallel surfaces within an ion confinement area or along paths in the direction of the electric field, or can be trapped in the ion confinement area. The surfaces are housed in a chamber, and at least one electrically insulative shield is coupled to an inner surface of the chamber for increasing a mean-free-path between two adjacent electrodes in the chamber.

21 Claims, 16 Drawing Sheets

(56) References Cited

U.S. PATENT DOCUMENTS

| | | |
|---|---|---|
| 7,838,826 B1 | 11/2010 | Park |
| 7,888,635 B2 | 2/2011 | Belov et al. |
| 8,049,169 B2 | 11/2011 | Satake et al. |
| 8,222,597 B2 | 7/2012 | Kim et al. |
| 2004/0026611 A1 | 2/2004 | Bateman et al. |
| 2007/0138384 A1 | 6/2007 | Keiser |
| 2011/0049357 A1 | 3/2011 | Giles |
| 2011/0192969 A1 | 8/2011 | Verentchikov |
| 2014/0145076 A1* | 5/2014 | Park .............. 250/290 |

OTHER PUBLICATIONS

PCT Recordation of Search History for International Application No. PCT/US14/11291, International Filing Date Jan. 3, 2014, Date during which the search was conducted May 15, 2014, Date of Completion of Recordation of Search History Form May 22, 2014.

* cited by examiner

ION MANIPULATION DEVICE WITH ELECTRICAL BREAKDOWN PROTECTION

CROSS-REFERENCE TO RELATED APPLICATIONS

This application is a continuation-in-part of U.S. application Ser. No. 14/146,922, filed Jan. 3, 2014, which claims the benefit of U.S. Provisional Application No. 61/809,660, filed Apr. 8, 2013, and both are incorporated herein by reference.

STATEMENT REGARDING FEDERALLY SPONSORED RESEARCH OR DEVELOPMENT

The invention was made with Government support under Contract DE-AC05-76RLO1830, awarded by the U.S. Department of Energy. The Government has certain rights in the invention.

TECHNICAL FIELD

This invention relates to ion manipulations in gases. More specifically, this invention relates to the use of RF and/or DC fields to manipulate ions through electrodes, and building complex sequences of such manipulations in devices that include one or more such surfaces and structures built upon the surfaces.

BACKGROUND OF THE INVENTION

As the roles for mass spectrometry and other technologies that involve the use, manipulation or analysis of ions continue to expand, new opportunities can become limited by approaches currently used for extended sequences of ion manipulations, including their transport through regions of elevated pressure, reaction (both ion-molecule and ion-ion), and ion mobility separations. As such manipulations become more sophisticated, conventional instrument designs and ion optic approaches become increasingly impractical, expensive and/or inefficient.

SUMMARY OF THE INVENTION

The present invention is directed to devices and methods of manipulating ions in gases. In one embodiment, an ion manipulation device is disclosed that is essentially lossless and allows extended sequences of ion manipulations. The device includes a pair of surfaces and in which a pseudopotential is formed that inhibits charged particles from approaching either of the surfaces, and the simultaneous application of DC potentials to control and restrict movement of ions between the surfaces.

In one implementation this involves two substantially or identical surfaces that have an inner array of electrodes, surrounded by a first outer array of electrodes and a second outer array of electrodes. Each outer array of electrodes is positioned on either side of the inner electrodes and contained within—and extending substantially along the length of—each parallel surface in a fashion similar to the inner array of electrodes. The DC potentials are applied to the first and second outer array of electrodes. The RF potentials, with a superimposed electric field, are applied to the array of inner electrodes.

The superimposed electric field may be a static or dynamic electric field. The static electric field may be, but is not limited to, a DC gradient. The dynamic electric field may be, but is not limited to, a traveling wave.

In one embodiment, the electrode arrangements on the two surfaces are identical, such that similar or identical voltages are applied to both. However, the exact arrangement of electrodes can differ, and the precise voltages applied to the two facing surfaces can also differ.

The pair of surfaces may be substantially planar, substantially parallel or parallel, or not flat.

In one embodiment, the RF potentials are applied along with the DC potentials on the first and second outer electrode arrays. In another embodiment, the RF potentials are applied to only one of the two surfaces. In another embodiment, the RF potentials are applied to both of the surfaces.

In one embodiment, the electric field in all or a portion of the device may be replaced with a gas flow to move ions in the direction of the gas flow.

In one embodiment, the RF on at least one inner electrode is out of phase with its neighboring inner electrode. In one embodiment the RF on each electrode is phase shifted with its neighboring inner electrode to form a repulsive pseudopotential. In one embodiment, the RF on each electrode is approximately 180 degrees out of phase with its neighboring inner electrode to form the pseudopotential.

In one embodiment, the array of inner electrodes comprises at least two electrodes on the pair of surfaces. In another embodiment, the first outer array of electrodes and the second outer array of electrodes each comprise at least two electrodes on the pair of surfaces. The device can include insulating material or resistive material between the electrodes.

The RF voltage applied to the electrodes is between 0.1 kHz and 50 MHz, the electric field is between 0 and 5000 volts/mm, and operating pressures from less than $10^{-3}$ torr to approximately atmospheric pressure or higher.

In one embodiment, the electrodes are perpendicular to at least one of the surfaces. In an alternative embodiment, the electrodes are parallel to at least one of the surfaces. The electrodes may comprise a thin conductive layer on the surfaces.

In certain embodiments, the device comprises multiple pairs of surfaces and allows transfer of the ions through an aperture to move between different pairs of surfaces.

The electrodes on the pair of surfaces may form one or more different configurations. These configurations include, but are not limited to, the following: a substantially T-shaped configuration, allowing ions to be switched at a junction of the T-shaped configuration; a substantially Y-shaped configuration, allowing ions to be switched at a junction of the Y-shaped configuration; a substantially X-shaped or cross-shaped configuration, allowing ions to be switched at a junction of one or more sides of the X-shaped or cross-shaped configuration; and/or a substantially multidirectional shape, such as an asterisk (*)-shaped configuration, with multiple junction points, allowing ions to be switched at a junction to one or more sides of the configuration.

In one embodiment, the electric field allows the ions to move in a circular-shaped path, rectangular-shaped path, or other irregular path, to allow the ions to make more than one transit and, as one example, achieve higher resolution ion mobility separations.

The space between the surfaces may be filled with an inert gas or a gas that ions react with ions.

Stacks of cyclotron stages may be used with the device to, for example, allow different ranges of ion mobilities to be separated in different cyclotron stages, and in sum cover the entire range of ions in a mixture.

The electric fields can be increased to cause ions to react or dissociate.

The device may be coupled to at least one of the following: a charge detector, an optical detector, and/or a mass spectrometer.

In one embodiment, the device can be fabricated and assembled using printed circuit board technology and interfaced with a mass spectrometer.

The device can be used to perform ion mobility separations and/or differential ion mobility separations (e.g., FAIMS).

Ions may be formed outside or inside the device using photoionization, Corona discharge, laser ionization, electron impact, field ionization, electrospray, or any other ionization technique that generates ions to be used with the device.

In another embodiment of the present invention, an ion manipulation device is disclosed. The device includes a pair of substantially parallel surfaces. The device further includes an array of inner electrodes contained within, and extending substantially along the length of, each parallel surface. The device also includes a first outer array of electrodes and a second outer array of electrodes, each positioned on either side of the inner electrodes, contained within, and extending substantially along the length of, each parallel surface, wherein a pseudopotential is formed that inhibits charged particles from approaching either of the parallel surfaces. The device also includes a RF voltage source and DC voltage sources, wherein a first DC voltage source is applied to the first and second outer array of electrodes and wherein a RF frequency, with a superimposed electric field, is applied to the inner electrodes by applying a second DC voltage to each electrode, such that ions move between the parallel surfaces within an ion confinement area in the direction of the electric field or can be trapped in the ion confinement area.

In one embodiment, the RF frequency applied to the electrodes is between 0.1 kHz and 50 MHz. The RF peak-to-peak voltage is approximately 10 to 2000 volts. The electric field is between about 0 and about 5000 volts/mm, and the pressure is between $10^{-3}$ torr and atmospheric pressure.

In one embodiment, one or more of the electrodes has 0.5 to 10 mm relief from the surface, so that degradation of device performance due to charging of the surfaces between electrodes is prevented.

In another embodiment of the present invention, a method of manipulating ions is disclosed. The method includes injecting ions between a pair of substantially parallel surfaces, wherein each pair of parallel surfaces contains an array of inner electrodes and a first and second array of outer electrodes on either side of the inner electrodes. The method further includes applying RF fields to confine the ions between the surfaces. The method also includes applying a first DC field to the outer electrodes equal to or higher than a second DC field applied to the inner electrodes to confine ions laterally. The method also includes superimposing the second DC field on the RF field to further confine and move the ions along in a direction set by the electric field.

In one embodiment, the method further includes transferring the ions through an aperture in at least one of the pairs of parallel surfaces, wherein the ions travel to between another pair of parallel surfaces.

In another embodiment of the present invention, an ion manipulation device is disclosed. The device includes multiple pairs of substantially parallel surfaces. The device further includes an array of inner electrodes contained within, and extending substantially along the length of, each parallel surface. The device also includes a plurality of outer arrays of electrodes, wherein at least one outer array of electrodes is positioned on either side of the inner electrodes. Each outer array is contained within and extends substantially along the length of each parallel surface, forming a potential that can inhibit ions moving in the direction of the outer array of electrodes, and which works in conjunction with a pseudopotential created by potentials applied to the inner array of electrodes that inhibits charged particles from approaching either of the parallel surfaces. The device also includes a RF voltage source and a DC voltage source. A DC voltage is applied to the plurality of outer arrays of electrodes. The RF voltage, with a DC superimposed electric field, is applied to the inner electrodes by applying the DC voltage to each electrode, such that ions will move between the parallel surfaces within an ion confinement area in the direction of the electric field or have their motion confined to a specific area such that they are trapped in the ion confinement area. Transfer of the ions to another pair of parallel surfaces or through multiple pairs of parallel surfaces is allowed through an aperture in one or more of the surfaces.

In another embodiment of the present invention, the electrodes have significant relief from the surfaces. Regions of such relief can be used to alter the electric fields, or also to prevent effects due to charging of nonconductive regions between electrodes. Such designs have particular value in regions where ion confinement is imperfect, such as in reaction regions where ion-molecule or ion-ion reactions result in ion products that have m/z values either too high or too low for effective ion confinement. In such cases just the reaction regions may require electrodes that extend from the surfaces, and in such cases these regions may have different, often larger, spacing between the two surfaces.

In another embodiment of the present invention RF potentials having two or more distinct frequencies and different electric fields are co-applied to the arrays of electrodes on the two surfaces and with a pattern of application that creates a pseudopotential that inhibits charged particles from approaching one or both of the substantially parallel surfaces over a substantially greater m/z range than would be feasible with RF potentials of a single frequency.

In another embodiment of the present invention, each central or inner electrode is replaced by two or more electrodes with adjacent electrodes having different phase of the RF applied such that the traps formed for ions close to one of the surfaces are substantially reduced, resulting in improved performance such as a reduction of possible trapping effects or reduction in the m/z range that can be transmitted, particularly when ion currents near the upper limit are being transmitted.

In another embodiment of the present invention, an ion manipulation device with electrical breakdown protection is disclosed. The device includes a pair of surfaces including an ion inlet and an ion outlet. The device also includes arrays of electrodes coupled to the surfaces to which RF potentials are applied to at least one of the surfaces in order to create a pseudopotential that inhibits charged particles from approaching the surfaces. The device further includes simultaneous application of DC potentials to control and restrict movement of ions in between each pair of surfaces, wherein the surfaces are housed in a chamber. At least one electrically insulative shield is coupled to an inner surface of the chamber for increasing a mean-free path between two adjacent electrodes in the chamber. The ion manipulation device can be, but is not limited to, an ion mobility cyclotron device.

In one embodiment, the at least one insulative shield includes a first insulative shield enclosing at least a part of the inlet and a second insulative shield enclosing at least a part of the outlet. The first insulative and the second insulative shield may be made of, but not limited to, Teflon, polyether ether ketone (PEEK), or polycarbonate.

In another embodiment, the inner surface is a side plate, and the at least one insulative shield is coupled to the plate via a sealing member.

The sealing member is, but not limited to, an O-ring, adhesive, or sealant, and the at least one insulative shield includes electrical feedthrough housing.

In one embodiment, the device includes a plurality of ion manipulation devices.

The device with electrical breakdown protection can include a first insulation plate between each ion device inside of the chamber. The first insulation plate is made of, but not limited to, ceramic, Teflon, fiberglass, PEEK, or polycarbonate.

The device with electrical breakdown protection can include a top cover located above a top ion device in the chamber, and a bottom cover located below a bottom ion device. The top cover may include bolt holes for sealing purposes, and the bottom lid may include a metal plate with an insulation plate embedded on the metal plate.

In one embodiment, an inlet of each device is coupled to an ion source, and an outlet of each device is coupled to a mass spectrometer. The ion source may be, but is not limited to, an ion funnel or a dual ion funnel.

In another embodiment of the present invention, an ion manipulation device with electrical breakdown protection is disclosed. The device includes a pair of surfaces including an ion inlet and an ion outlet. The device also includes arrays of electrodes coupled to the surfaces to which RF potentials are applied to at least one of the surfaces in order to create a pseudopotential that inhibits charged particles from approaching the surfaces. The device further includes simultaneous application of DC potentials to control and restrict movement of ions in between each pair of surfaces, wherein the surfaces are housed in a chamber. At least one electrically insulative shield is coupled to a side plate of the chamber via a sealing member for increasing a mean-free-path between two adjacent electrodes in the chamber.

In another embodiment of the present invention, an ion manipulation device with electrical breakdown protection is disclosed. The device includes a pair of surfaces including an ion inlet and an ion outlet. The device also includes arrays of electrodes coupled to the surfaces to which RF potentials are applied to at least one of the surfaces in order to create a pseudopotential that inhibits charged particles from approaching the surfaces. The device further includes simultaneous application of DC potentials to control and restrict movement of ions in between each pair of surfaces, wherein the surfaces are housed in a chamber. A first insulative shield encloses at least part of the inlet and a second insulative shield encloses at least a part of the outlet.

In another embodiment of the present invention, an ion manipulation device with electrical breakdown protection is disclosed. The device includes a pair of surfaces including an ion inlet and an ion outlet. The device also includes arrays of electrodes coupled to the surfaces to which RF potentials are applied to at least one of the surfaces in order to create a pseudopotential that inhibits charged particles from approaching the surfaces. The device further includes simultaneous application of DC potentials to control and restrict movement of ions in between each pair of surfaces, wherein the surfaces are housed in a chamber. The device also includes a plurality of insulative shields for increasing a mean-free-path between two adjacent electrodes in the chamber, wherein the plurality of shields includes: i. one or more inner surface insulative shields coupled to one or more side plates of the chamber; and one or more inlet and outlet insulative shields, wherein the inlet insulative shield encloses at least a part of the inlet, and the outlet insulative shield encloses at least a part of the outlet.

DETAILED DESCRIPTION OF THE PREFERRED EMBODIMENTS

The present invention is directed to devices, apparatuses, and method of manipulating ions. The present invention uses electric fields to create field-defined pathways, traps, and switches to manipulate ions in the gas phase, and with minimal or no losses. Embodiments of the device enable complex sequences of ion separations, transfers, path switching, and trapping to occur in the space between two surfaces positioned apart and each patterned with conductive electrodes. In one embodiment, the present invention uses the inhomogeneous electric fields created by arrays of closely spaced electrodes to which readily generated peak-to-peak RF voltages ($V_{p-p}$~100 V; ~1 MHz) are applied with opposite polarity on adjacent electrodes to create effective potential or pseudopotential fields that prevent ions from approaching the surfaces. These ion confining fields result from the combination of RF and DC potentials, with the RF potentials among other roles creating a pseudopotential that prevents loss of ions and charged particles over certain m/z ranges to a surface, and the DC potentials among other roles being used to confine ions to particular defined paths of regions between the two surfaces, or to move ions parallel to the surfaces. The confinement functions over a range of pressures (<0.001 torr to ~1000 torr), and over a useful, broad, and adjustable mass to charge (m/z) range. Of particular interest is the ability to manipulate ions that can be analyzed by mass spectrometers, and where pressures of <0.1 to ~50 torr can be used to readily manipulate ions over a useful m/z range, e.g., m/z 20 to >5,000. This effective potential works in conjunction with DC potentials applied to side electrodes to prevent ion losses, and allows the creation of ion traps and/or conduits in the gap between the two surfaces for the effectively lossless storage and/or movement of ions as a result of any gradient in the applied DC fields.

In one embodiment, the invention discloses the use of RF and DC fields to manipulate ions. The manipulation includes, but is not limited to, controlling the ion paths, separating ions, reacting ions, as well as trapping and accumulating the ions by the addition of ions to the trapping region(s). The ion manipulation device, which may be referred to as an "ion conveyor" or Structure for Lossless Ion Manipulation (SLIM), uses arrays of electrodes on substantially parallel surfaces to control ion motion. Combinations of RF and DC potentials are applied to the electrodes to create paths for ion transfer and ion trapping. The parallel surfaces may be fabricated using, but not limited to, printed circuit board technologies or 3D printing.

Figure 1A:
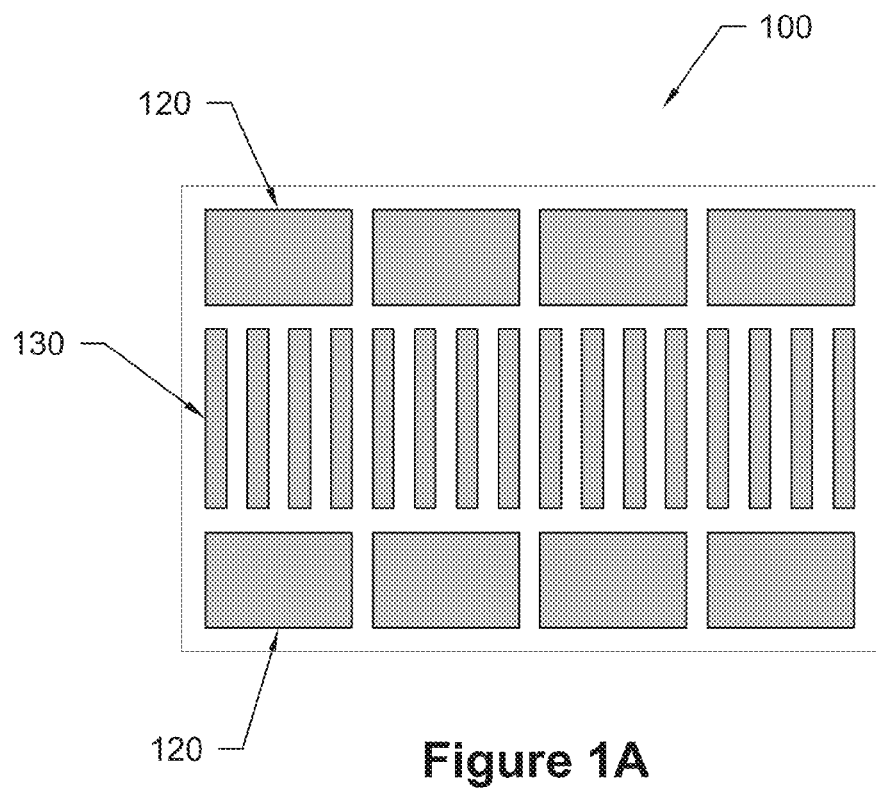
FIG. 1A is a schematic of a portion of an individual parallel surface containing an arrangement of electrodes for an ion manipulation device, in accordance with one embodiment of the present invention.

FIG. 1A is a schematic of a portion of an individual parallel surface 100 containing a first and second array of outer electrodes 120 and an array of inner electrodes 130 for an ion manipulation device, in accordance with one embodiment of the present invention. The array of inner electrodes 130 is contained within and extends substantially along the length of the surface 100. The array of outer electrodes 120, positioned on either side of the inner electrodes 130, is also contained within and extends substantially along the length of the surface 100.

Figure 1B:
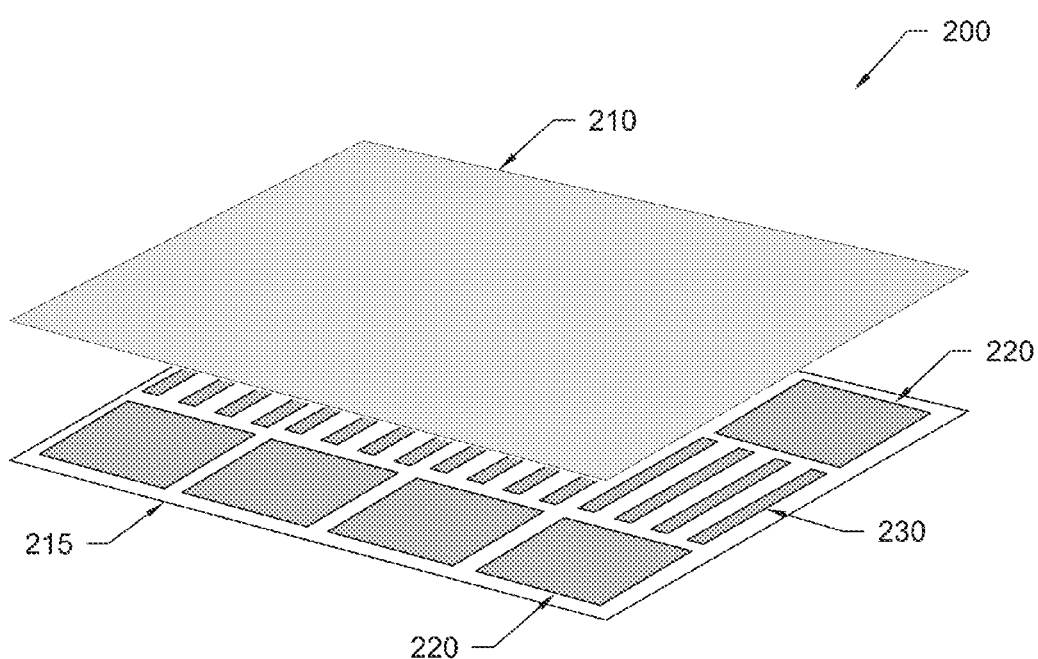
FIG. 1B is a schematic of a portion of an ion manipulation device, in accordance with one embodiment of the present invention.

FIG. 1B is a schematic of a portion of an ion manipulation device 200, in accordance with one embodiment of the present invention. The device 200 includes a pair of substantially parallel surfaces 210 and 215. Each surface contains an array of inner electrodes 230 and a first and second array of outer electrodes 220. The arrays of outer electrodes 220 are positioned on either side of the array of inner electrodes 230. The arrays of electrodes 220 and 230 are contained within and extend substantially along the length of each parallel surface 210 and 215. The arrangement of electrodes on the opposing surfaces can be identical as well as the electric field applied. Alternately, either the detailed electrode arrangements or the electric fields applied can be different in order to affect ion motion and trapping between the device.

Figure 2:
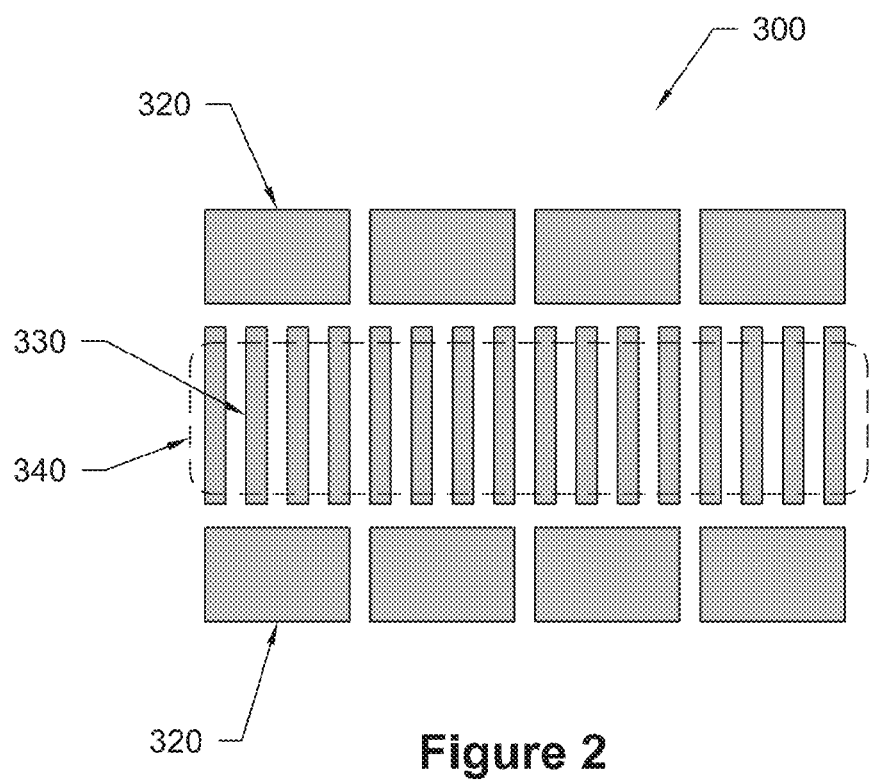
FIG. 2 is a schematic of a portion of an individual parallel surface containing an arrangement of electrodes, and also showing an ion confinement area, for an ion manipulation device, in accordance with one embodiment of the present invention.

The portion of the device 200 also includes a RF voltage source and DC voltage sources (not shown). In one embodiment, the DC voltages are applied to the first and second outer array of electrodes 220. The RF voltage, of opposite polarity upon adjacent electrodes, with a superimposed DC electric field, is applied to the inner array of electrodes 220. In the arrangement of FIG. 2, with the RF and DC fields applied as such, ions either move between the parallel surfaces 210 and 215 within an ion confinement area in the direction of the electric field or can be trapped in the ion confinement area depending on the DC voltages applied.

In one embodiment, the RF on at least one inner electrode is out of phase with its neighboring inner electrode. In another embodiment, each inner electrode is 180 degrees out of phase with its neighboring inner electrode to form a pseudopotential that inhibits charged particles from approaching either of the parallel surfaces. In another embodiment each inner electrode is replaced by two or more electrodes to which RF is applied to each and with one or more the electrodes being out of phase with its neighboring inner electrodes.

The electric field also allows the ions to move in a circular-shaped or a rectangular-shaped path, to allow the ions to make more than one transit. Stacks of cyclotron stages can be used with the device 200. Arrangements with cyclotrons, where the ions traverse a circular path, will allow very high-resolution mobility separations with small physical size.

In one embodiment, the array of inner electrodes 220 comprises at least two electrodes on the pair of parallel surfaces 210 and 215. The first outer array of electrodes and the second outer array of electrodes 220 may each comprise at least two electrodes on the pair of parallel surfaces 210 and 215.

In one embodiment the RF is simultaneously applied with DC potentials to the electrodes 220, and in another embodiment the RF applied to adjacent outer electrodes has opposite polarity.

In one embodiment the space between the surfaces 210 and 215 may include a gas or otherwise vaporized or dispersed species that ions react with.

In one embodiment the electrodes 220 are augmented by an additional set of electrodes further displaced from the central electrodes that has DC potentials applied that are opposite in polarity to allow the confinement or separation of ions of opposite polarity.

The device 200 can be coupled to other devices, apparatuses and systems. These include, but are not limited to, a charge detector, an optical detector, and/or a mass spectrometer. The ion mobility separation possible with the device 200 can be used for enrichment, selection, collection and accumulation over multiple separations of any mobility resolved species.

The device 200 may be used to perform ion mobility separations.

In one embodiment, the RF frequency applied to the electrodes 230 is between 0.1 kHz and 50 MHz, and the electric field is between 0 and 5000 volts/mm.

In one embodiment, the electrodes 220 and 230 are perpendicular to at least one of the surfaces and may comprise a thin conductive layer on the surfaces 210 and 215.

The device 200 can include multiple pairs of substantially parallel surfaces, allowing transfer of the ions through an aperture to move between different pairs of parallel surfaces.

The electrodes on the pair of surfaces 210 and 215 can form one of many different configurations. In one embodiment, the surfaces 210 and 215 form a substantially T-shaped configuration, allowing ions to be switched at a junction of the T-shaped configuration. In another embodiment, the surfaces 210 and 215 form a substantially Y-shaped configuration, allowing ions to be switched at a junction of the Y-shaped configuration. In another embodiment, the surfaces 210 and 215 form a substantially X-shaped or cross-shaped configuration, allowing ions to be switched at a junction or one or more sides of the X-shaped configuration. In another embodiment, the surfaces 210 and 215 form a substantially multidirectional shape, such as an asterisk (*)-shaped configuration, with multiple junction points, allowing ions to be switched at a junction to one or more sides of the configuration. Devices may be constituted from any number of such elements.

The electrodes on the surfaces can have any shape, not being limited to the rectangular shapes such as in FIG. 1. For example, the electrodes can be round, have ellipse or oval shapes, or be rectangles with rounded corners.

FIG. 2 is a schematic of an individual parallel surface 300 containing an arrangement of electrodes 320 and 330 with an ion confinement area 340 for an ion manipulation device, in accordance with one embodiment of the present invention. Static DC voltages may be applied to the outer electrodes 320 with RF applied to the inner electrodes 330. Each central electrode can have RF applied out of phase with its neighboring electrode.

A DC or other electric field is superimposed on the RF and applied to the inner electrodes 330 to move ions through the device of FIG. 2, in addition to successively lower voltages applied on each outer electrode 320—moving from left to right or alternatively from right to left, depending on the polarity and the desired direction of motion. This electric field forces ions to the right, while the RF and DC fields also confine ions to a central region of the device as shown. Voltage polarities can be changed to allow manipulation of both negative and positive ions.

Figure 3A:
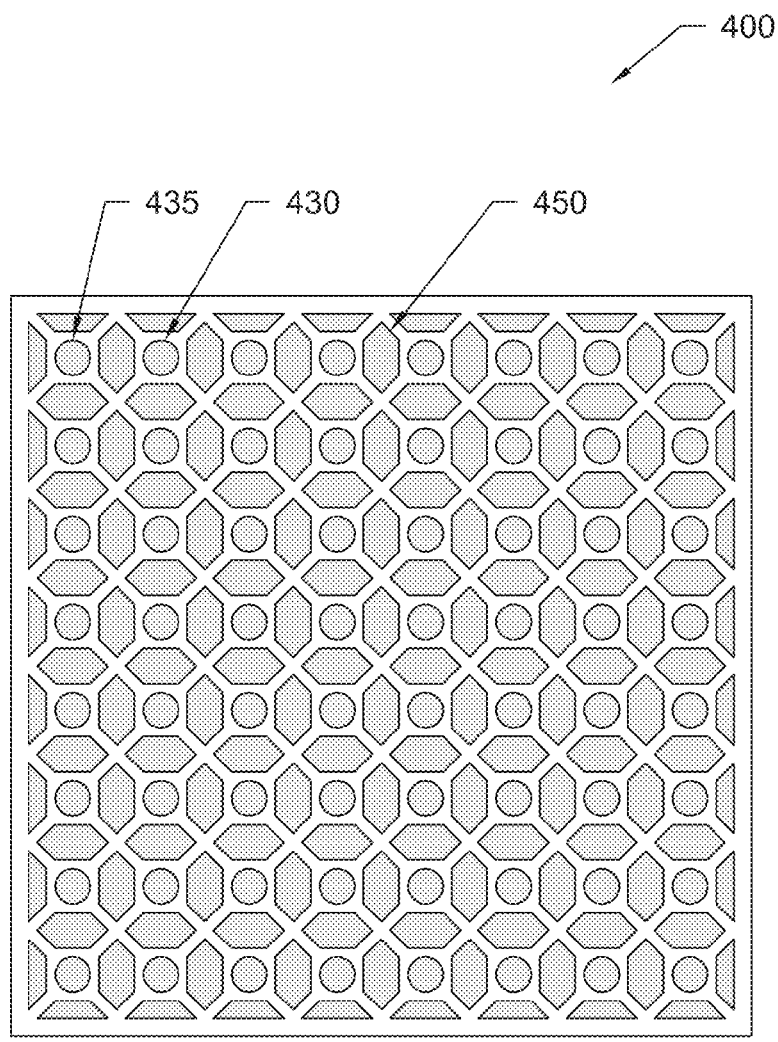
FIG. 3A is a schematic of an individual parallel surface containing an arrangement of electrodes for an ion manipulation device, in accordance with one embodiment of the present invention.

FIG. 3A is a schematic of an individual parallel surface 400 containing an arrangement of electrodes for an ion manipulation device, in accordance with one embodiment of the present invention. The surface 400 includes electrodes 450 that are individually programmable by a DC voltage, electrodes 430 associated with a negative RF voltage, and electrodes 435 associated with a positive RF voltage—where negative and positive RF refers to the phase of the RF waveform.

Figure 3B:
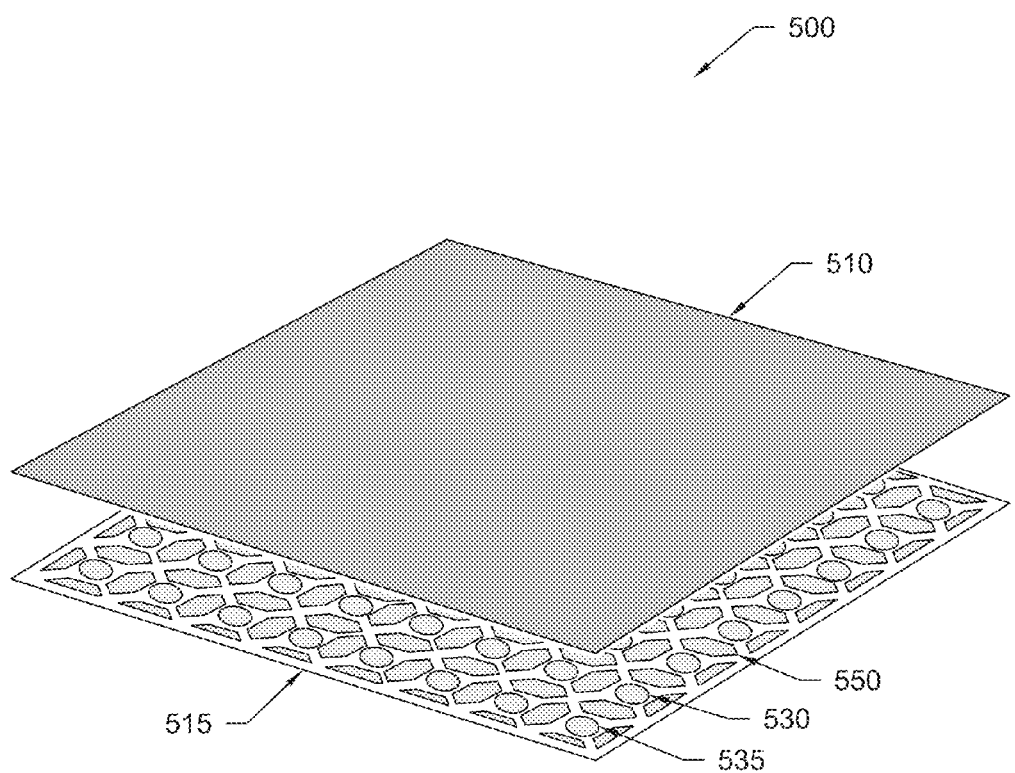
FIG. 3B is a schematic of an ion manipulation device, in accordance with one embodiment of the present invention.

FIG. 3B is a schematic of an ion manipulation device 500, in accordance with one embodiment of the present invention. The ion manipulation device 500 includes substantially parallel surfaces 510 and 515 that are similar to the surface 400 of FIG. 3A. The device 500 includes electrodes 550 that are individually programmable by a DC voltage, electrodes 530 associated with a negative RF voltage, and electrodes 535 associated with a positive RF voltage. In this arrangement, ions are confined between the surfaces 510 and 515. The ions move in the direction defined by an electric field.

Figure 4A:
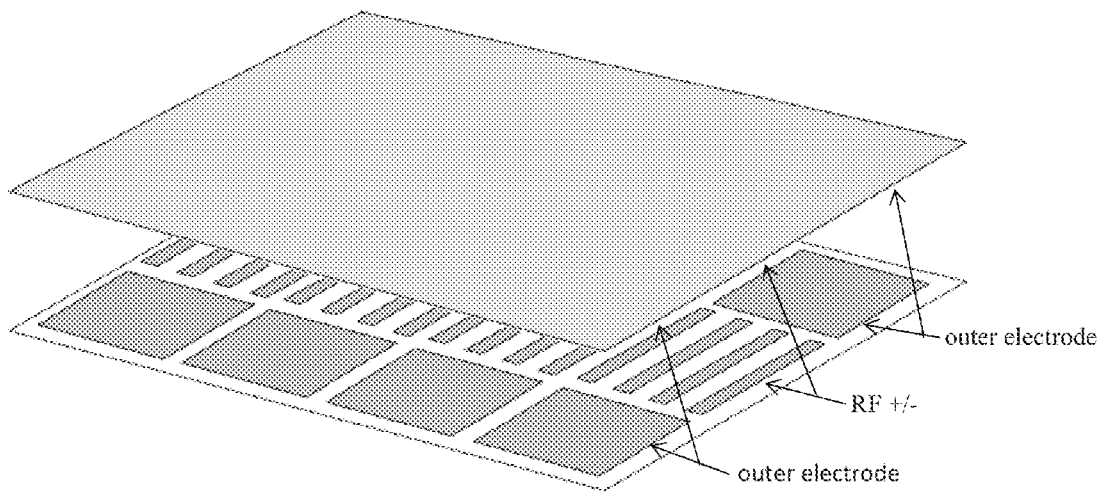
FIG. 4A is a schematic of an ion manipulation device, in accordance with one embodiment of the present invention.

FIG. 4A is a schematic of an ion manipulation device, in accordance with one embodiment of the present invention. The central or inner electrodes have RF fields applied with opposite polarity to adjacent electrodes to create fields that prevent ions from closely approaching the surfaces. Ions are moved according to their mobilities under DC fields applied to the outer electrodes.

Figure 4B:
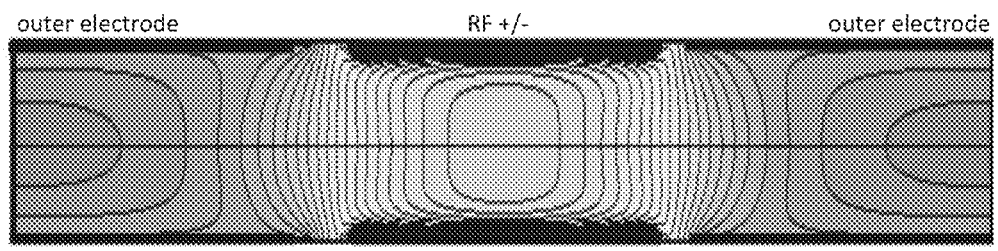
FIG. 4B shows where the ions will be confined when DC and RF potentials are applied to the device of FIG. 4A, in accordance with one embodiment of the present invention.

FIG. 4B shows the trapping volume of ions between the surfaces containing electrodes of an ion manipulation device, in accordance with one embodiment of the present invention. Both positive and negative charged ion particles are confined in overlapping areas of the ion manipulation device. This can be accomplished using multiple arrays of outer electrodes and applying both RF and DC potentials.

The devices of the present invention provide for at least the following: lossless (a) linear ion transport and mobility separation, (b) ion transport around a corner (e.g., a 90 degree bend), (c) ion switches to direct ions to one of at least two paths, (d) ion elevators for transporting ions between different levels of multilevel ion manipulation devices, (e) ion traps for trapping, accumulation, and reaction of ions of one polarity. These devices can be combined to create a core module for more complex ion manipulation devices such as an ion mobility cyclotron. In one implementation, integrating several modules will allow fabrication of a single level device that will enable the separation of ions over periods on the order of 0.1 to 10 seconds while achieving resolutions of up to approximately 1000 for species over a limited range of mobilities. The range of mobilities, and the fractions of the total biomolecule ion mixture that can be separated, decreases as the resolution is increased. Thus, an ion mobility cyclotron module can provide a useful and targeted separation/analysis capability—where information is desired for a limited subset of species.

The integrated device can consist of a stack of modules each covering a different portion of the full mobility spectrum. In combination, they provide separations that cover the full range of ion mobilities needed for a sample, while at the same time making efficient use of all the ions from the sample. The integrated device can draw upon the ion switch, elevator, and trap components to provide a low resolution separation that partitions ions from the sample into fractions that are delivered to different cyclotrons using the ion elevator.

Figure 5A:
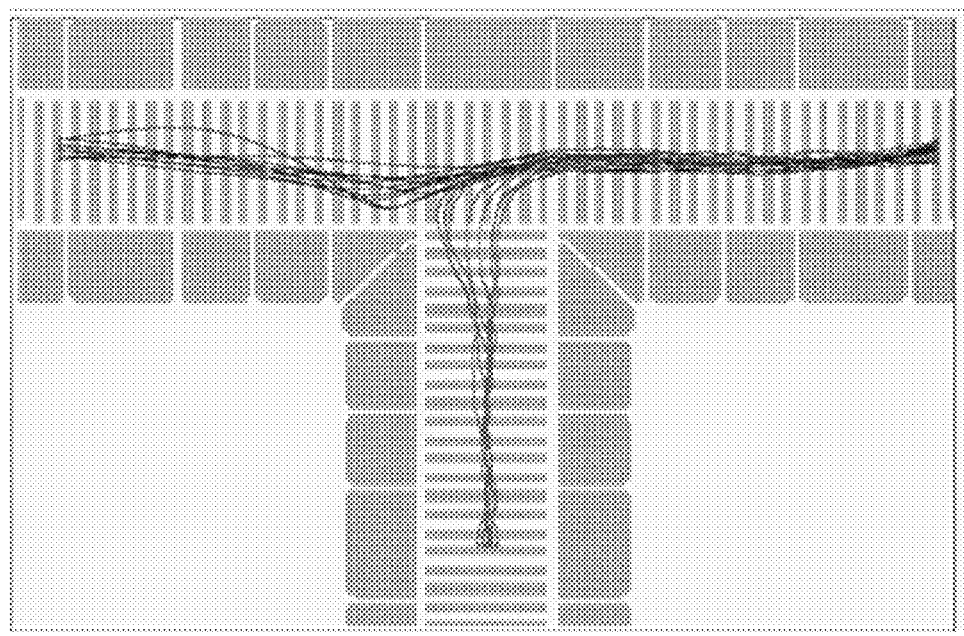
FIGS. 5A, 5B, and 5C show simulations for an ion switch in a T-shaped configuration of an ion manipulation device, in accordance with one embodiment of the present invention.
Figure 5B:
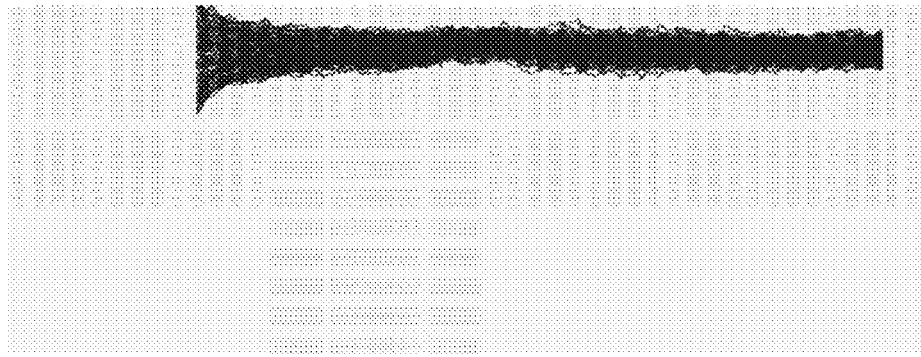
Figure 5C:
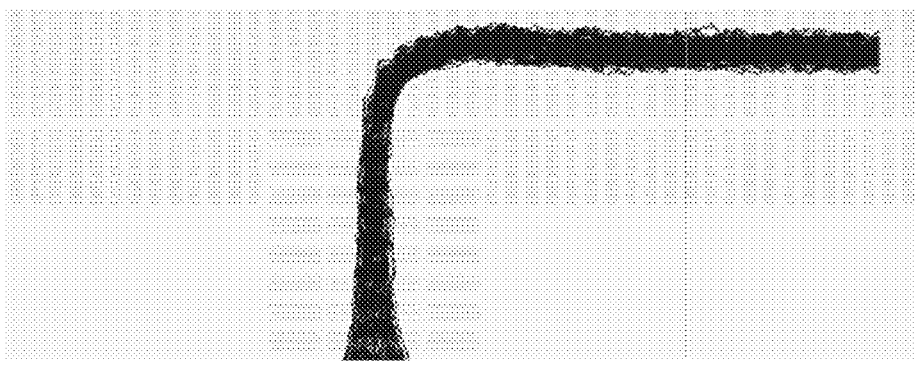

FIGS. 5A, 5B, and 5C show simulations of an ion switch in a T-shaped configuration of an ion manipulation device, in accordance with one embodiment of the present invention. These ion paths can be controlled using switch elements. As shown in FIGS. 5A, 5B, and 5C, the ion path can be dynamically or statically changed by modifying the electrode arrangement of the device and/or varying the RF and DC voltages. The ions can be switched at a junction as shown in FIG. 5A, move in a straight path as shown in FIG. 5B, and/or curve or bend around a corner at the junction as shown in FIG. 5C. Alternatively, the pair of parallel surfaces of the device can form other configurations such as, but not limited to, Y-shaped configurations, X-shaped or cross-shaped configurations, and other multidirectional shapes.

Figure 6:
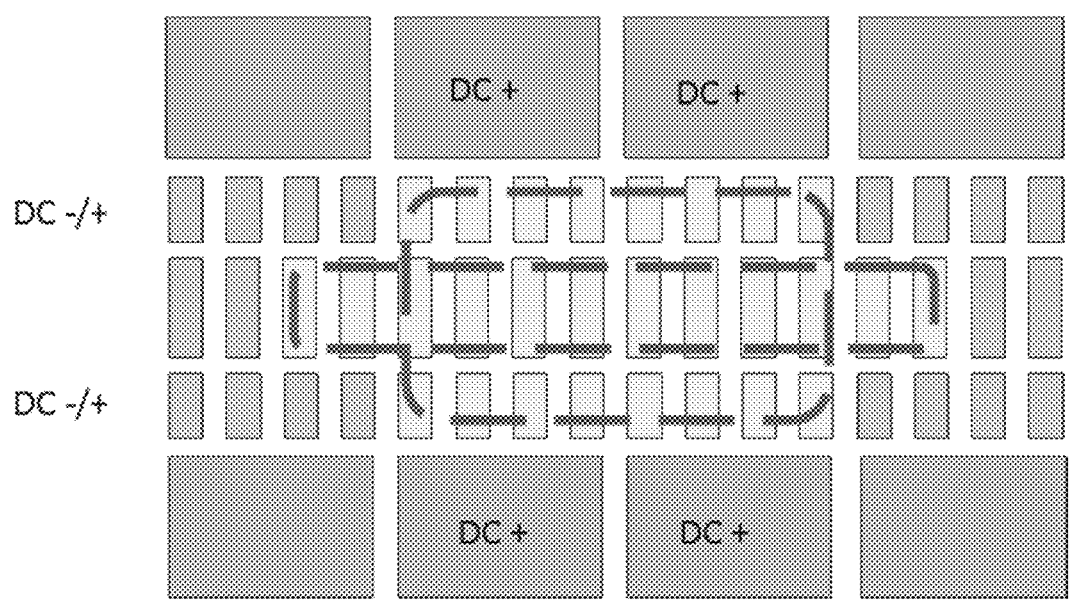
FIG. 6 shows dual polarity trapping regions for ion-ion reactions in an ion manipulation device, in accordance with one embodiment of the present invention.

FIG. 6 shows dual polarity trapping regions for ion-ion reactions in an ion manipulation device, in accordance with one embodiment of the present invention. Different polarity of ions, positive and negative, can be trapped at the same time in at least partially overlapping physical volumes between the two surfaces of the device using multiple sets of electrodes and applying both RF and DC potentials. Additional RF or DC potentials can be applied to heat and excite either the positive or negatively charged ions in order to change the reaction rate or reaction products.

Figure 7:
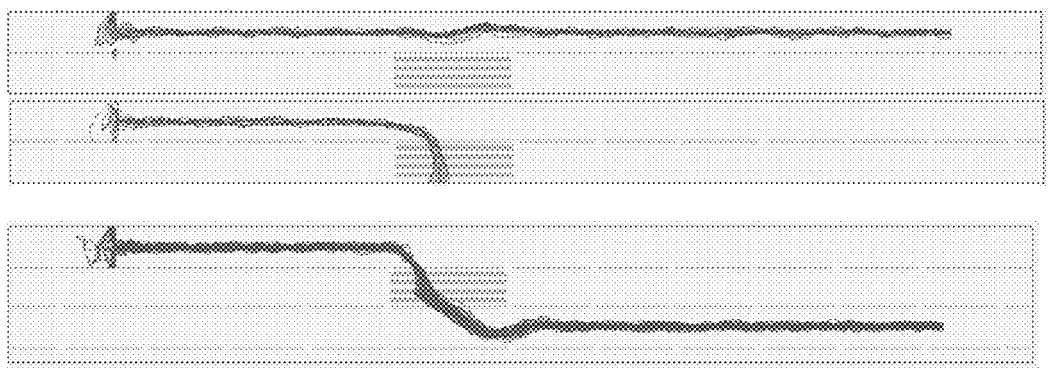
FIG. 7 shows simulations of an ion switch in an "elevator" configuration where ions are transferred through one or more apertures to move between different pairs of parallel surfaces in an ion manipulation device, in accordance with one embodiment of the present invention.

FIG. 7 shows simulations of an ion switch in an "elevator" configuration where ions are transferred through one or more apertures to move between different pairs of parallel surfaces in an ion manipulation device, in accordance with one embodiment of the present invention. This allows multi-dimensional ion manipulation using the ion manipulation device. In some embodiments additional electrodes are added to increase the efficiency of transfer between different levels, including electrodes with DC and/or RF potentials with different polarities on adjacent electrodes.

Figure 8:
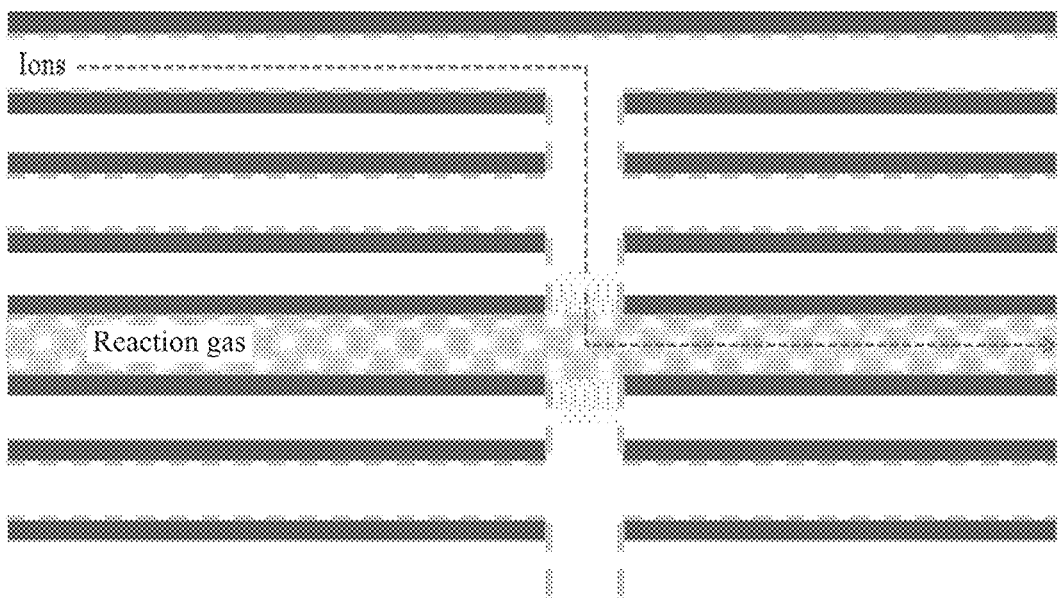
FIG. 8 shows simulations of an ion switch in an "elevator" configuration having multiple levels where ions are transferred through one or more apertures to move between different pairs of parallel surfaces in an ion manipulation device, in accordance with one embodiment of the present invention.

FIG. 8 shows simulations of an ion switch in an "elevator" configuration having multiple levels where ions are transferred through one or more apertures to move between different pairs of parallel surfaces in an ion manipulation device, in accordance with one embodiment of the present invention.

Figure 9:
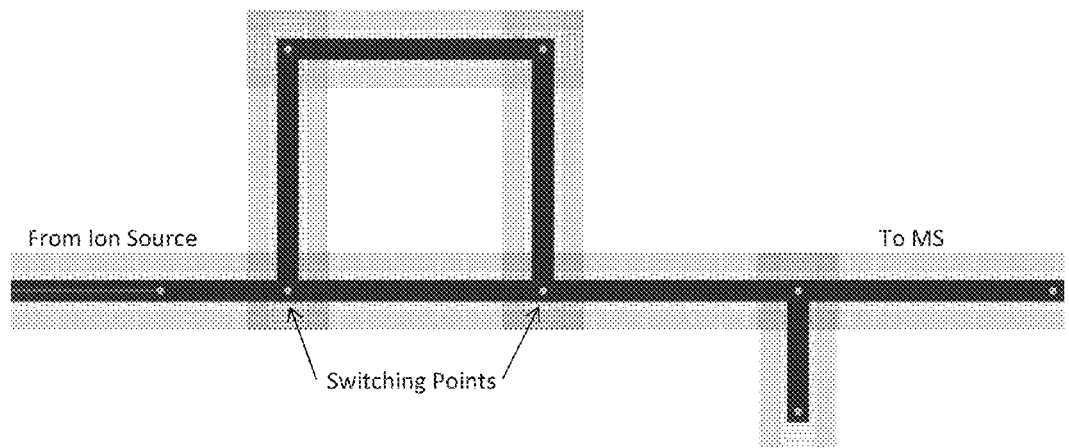
FIG. 9 shows an ion manipulation device implemented as an ion mobility cyclotron for high resolution separations, in accordance with one embodiment of the present invention.

FIG. 9 is a schematic showing an ion manipulation device implemented as an ion mobility cyclotron. Ions entering from the ion source are initially trapped before a first low resolution separation. Separated ions of interest are trapped and then injected for cyclotron separations, potentially achieving resolutions greater than 1000. The switching points direct ions to one of at least two paths. All four points—the switching points and the bends—are where changes in the rotating DC electric field can be applied to create the cyclotron motions.

Figure 10:
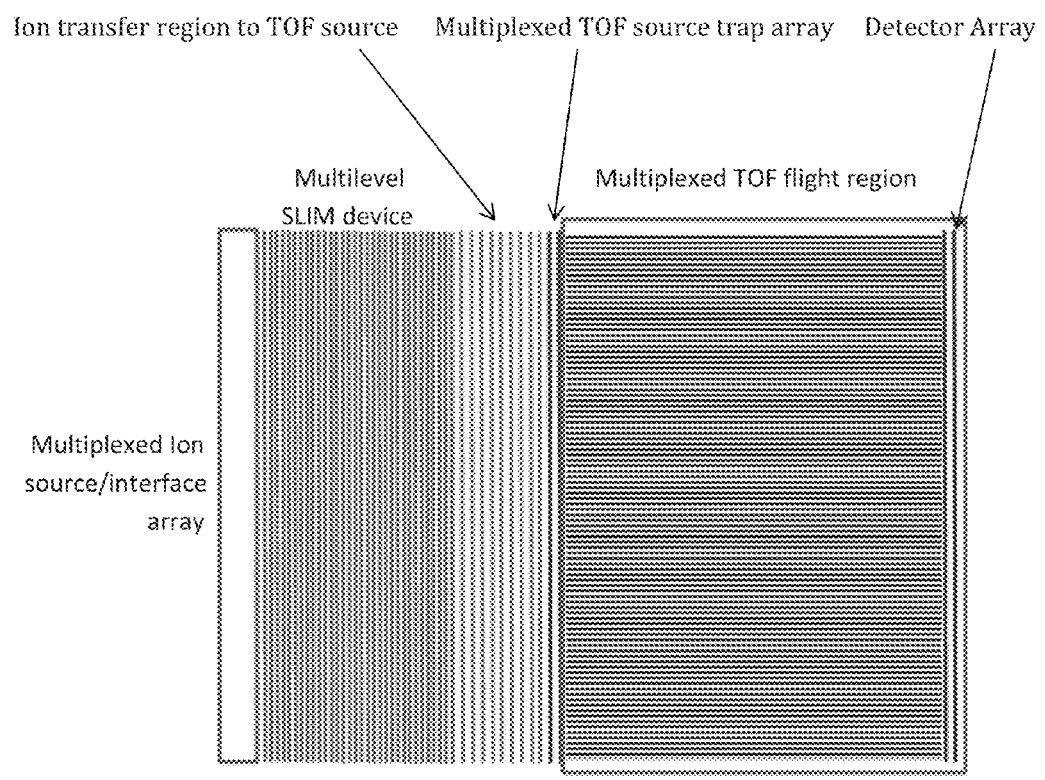
FIG. 10 shows an ion mobility device coupled between an array of ion sources and an array of mass spectrometer devices, in accordance with one embodiment of the present invention.

FIG. 10 shows an ion mobility device coupled between an array of ion sources and an array of mass spectrometer devices, in accordance with one embodiment of the present invention. As shown in FIG. 10, the present invention also enables multiplexed sample analyses using an array of ion sources and multiple ion separations in parallel—separated during travel through the device—and detected using an array of high speed, high dynamic range time-of-flight (TOF) mass spectrometers (MS).

The pair of surfaces of the ion manipulation device can be housed in a vacuum chamber. In one embodiment, at least one electrically insulative shield is coupled to an inner surface of the chamber for increasing a mean-free-path between two adjacent electrodes in the chamber.

Figure 11:
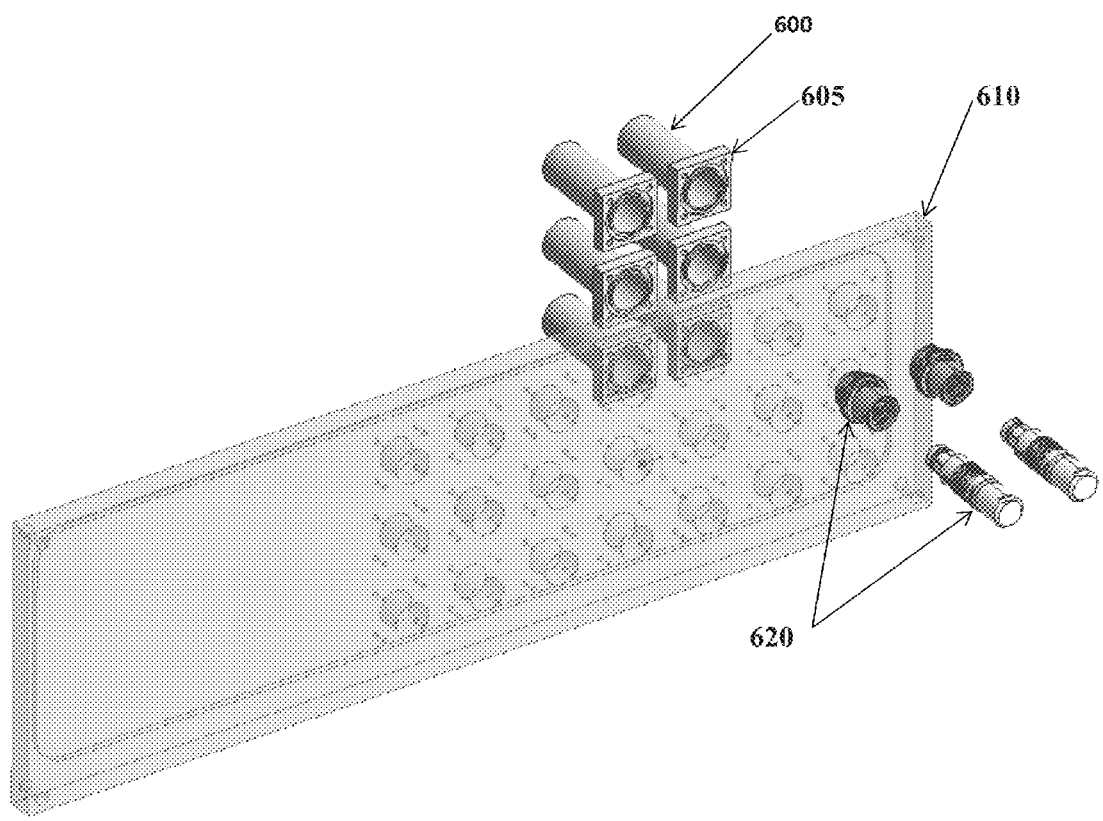
FIG. 11 shows one example of an electrical interface for an ion manipulation device in a chamber, including a side lid, electrical insulation housings and electrical feedthroughs, in accordance with one embodiment of the present invention.

FIG. 11 shows one example of an electrical interface for an ion manipulation device in a chamber, including a side lid 610, electrical insulation housings 600 and electrical feedthroughs 620, in accordance with one embodiment of the present invention. The side lid is made of a nonconductive material. The bottom or flange side 605 of the electrical insulation housing 600 includes a sealing member to isolate the mean-free-path between adjacent electrodes on the chamber side of the feedthroughs 620. The sealing member is, but not limited to, an O-ring, an adhesive, or a sealant. The flange 605 is coupled to the side lid 610 via the sealing member.

Figure 12:
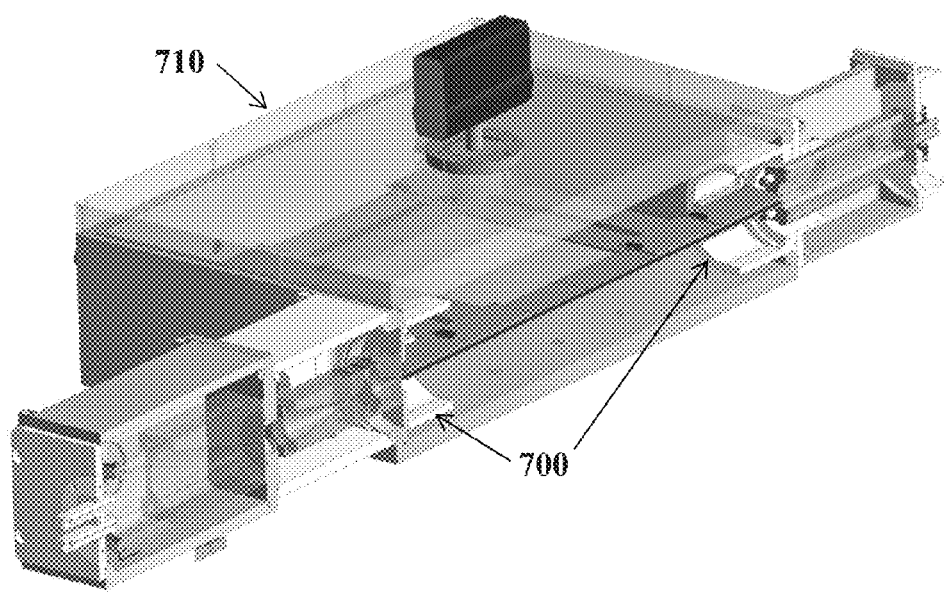
FIG. 12 shows one example of an insulation shield coupled to inlet and outlet openings of an ion manipulation device inside of a chamber, in accordance with one embodiment of the present invention.

FIG. 12 shows one example of an insulation shield 700 coupled to inlet and outlet openings of an ion manipulation device inside of a chamber 710, in accordance with one embodiment of the present invention. The insulation shield 700 is made of, but not limited to, Teflon, PEEK, or polycarbonate.

Figure 13:
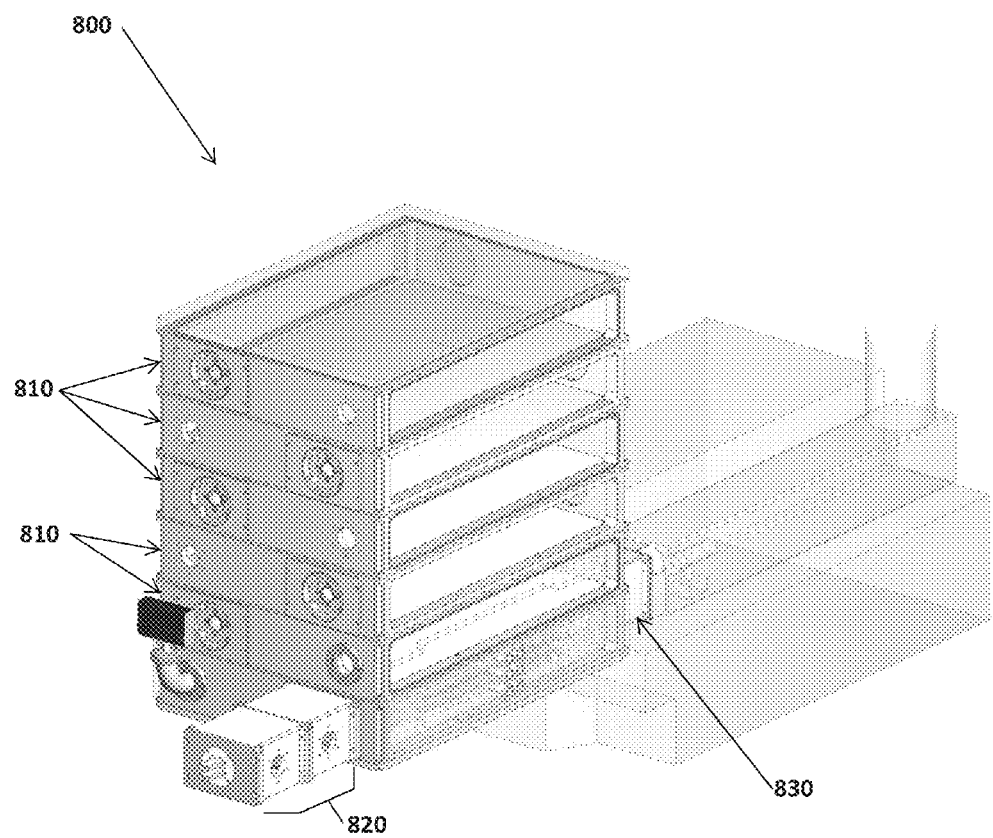
FIG. 13 shows a plurality of vacuum chambers arranged in a stack for housing one or more ion manipulation devices, in accordance with one embodiment of the present invention.

FIG. 13 shows a plurality of vacuum chambers 810 arranged in a stack 800 for housing one or more ion manipulation devices, in accordance with one embodiment of the present invention. Although six chambers are shown in FIG. 13, it should be noted that the stack 800 is not limited to any specific number of chambers.

The chambers 810 include at least one inlet and at least one outlet. The inlet may be coupled to an ion source interface such as, but not limited to, an ion funnel or a dual ion funnel 820. The outlet may be coupled to a mass spectrometer or analyzer directly or indirectly via another ion device 830 for manipulating and/or focusing ions. In the embodiment of FIG. 13, the bottom chamber of the stack 800 is coupled through an ion funnel chamber 820 to a mass spectrometer 830 at the outlet. In the inlet, two ion funnel chambers 820 are connected as the ion source interface. One or more of the chambers 810 can include a sensor such as, but not limited to, a pressure sensor.

EXAMPLE

The following examples serve to illustrate certain embodiments and aspects of the present invention and are not to be construed as limiting the scope thereof A device, as shown in FIG. 1B, was used to manipulate ions injected from an external ESI source. Simulations were performed to refine the design of the device; e.g. electrode sizes and spacing between the planar surfaces were adjusted. Boards were fabricated with electrode regions to test capabilities that included efficient ion transportation, ion mobility separations, ion trapping, and ion switching between alternative corridors or paths.

In one test, ions were introduced from the external ESI source and injected into one of the ion corridors at a pressure of ~4 torr. RF frequencies of approximately 1.4 MHz and 140 Vp-p were applied to create repulsive fields to confine ions within the ion corridors between the opposing board surfaces. The RF fields were combined with DC for further confinement to the corridors and also to move the ions along the corridors based upon their ion mobilities. Separate electrodes were used to measure ion currents at various locations and evaluate ion transmission efficiency through different areas of the device. Initial measurements showed that ions can be efficiently introduced into such devices, as well as transported through them with minimal losses.

The device of the present invention, including its various embodiments, can be manufactured at very low cost and is very flexible, allowing application to many different areas in mass spectrometry. As one example, the device can be fabricated and assembled using printed circuit board technology and interfaced with a mass spectrometer. The device can also be lossless. Ion mobility separation and complex ion manipulation strategies can be easily implemented with the device.

The device of the present invention, including its various embodiments, can be altered in its performance by the use of electrodes that have significant thickness and thus substantial relief from one or both of the surfaces. The thickness can vary between electrodes, and individual electrodes can have variable thickness. These electrodes can be used to create electric fields not practical for very thin electrodes (e.g. surface deposited such as on conventional printed circuit boards). Regions of devices with such electrodes have particular value when incomplete or inefficient ion confinement may occur, such as for very low or high m/z ions created by reactions that can provide a well-controlled electric field and prevent degraded performance from distorted electric fields due to the charging of surfaces between electrodes.

Embodiments of the present invention can improve and extend analysis capabilities in, for example, proteomics, metabolomics, lipidomics, glycomics, as well as their applications to a broad range of biological and chemical measurements and applicable research areas. Utilization of the ion manipulation device can lead to faster, cheaper, and more sensitive measurements relevant to understanding chemical, environmental, or biological systems. The present invention enables MS-based approaches involving complex ion manipulations in the gas phase capable of augmenting or completely displacing conventional liquid phase approaches. The present invention also enables separations and other ion manipulations over extended periods in a nearly lossless fashion. These capabilities lead to very fast and high resolution gas phase separations of ions.

The present invention has been described in terms of specific embodiments incorporating details to facilitate the understanding of the principles of construction and operation of the invention. As such, references herein to specific embodiments and details thereof are not intended to limit the scope of the claims appended hereto. It will be apparent to those skilled in the art that modifications can be made in the embodiments chosen for illustration without departing from the spirit and scope of the invention.

We claim:

1. An ion manipulation device with electrical breakdown protection comprising:
   a. a pair of surfaces including an ion inlet and an ion outlet;
   b. arrays of electrodes coupled to the surfaces to which RF potentials are applied to at least one of the surfaces in order to create a pseudopotential that inhibits charged particles from approaching the surfaces; and
   c. simultaneous application of DC potentials to control and restrict movement of ions in between each pair of surfaces, wherein the surfaces are housed in a chamber; and
   d. at least one electrically insulative shield coupled to an inner surface of the chamber for increasing a mean-free-path between two adjacent electrodes in the chamber.

2. The device of claim 1 wherein the ion manipulation device is an ion mobility cyclotron device.

3. The device of claim 2 further comprising a plurality of ion devices.

4. The device of claim 3 further comprising a first insulation plate between each ion device inside of the chamber.

5. The device of claim 4 wherein the first insulation plate is made of ceramic, Teflon, fiberglass, PEEK, or polycarbonate.

6. The device of claim 5 further comprising a top cover located above a top ion device in the chamber, and a bottom cover located below a bottom ion device.

7. The device of claim 6 wherein the top cover includes bolt holes for sealing purposes.

8. The device of claim 6 wherein the bottom cover includes a metal plate and an insulation plate embedded on the metal plate.

9. The device of claim 3 wherein an inlet of each device is coupled to an ion source and an outlet of each device is coupled to a mass spectrometer.

10. The device of claim 9 wherein the ion source is an ion funnel or a dual ion funnel.

11. The device of claim 1 wherein the at least one insulative shield includes a first insulative shield enclosing at least a part of the inlet and a second insulative shield enclosing at least a part of the outlet.

12. The device of claim 11 wherein the first insulative shield and the second insulative shield are made of Teflon, polyether ether ketone (PEEK), or polycarbonate.

13. The device of claim 1 wherein the inner surface is a side plate, and the at least one insulative shield is coupled to the plate via a sealing member.

14. The device of claim 13 wherein the sealing member is an O-ring, adhesive, or sealant, and the at least one insulative shield includes electrical feedthrough housing.

15. An ion manipulation device with electrical breakdown protection comprising:
   a. a pair of surfaces including an ion inlet and an ion outlet;
   b. arrays of electrodes coupled to the surfaces to which RF potentials are applied to at least one of the surfaces in order to create a pseudopotential that inhibits charged particles from approaching the surfaces; and
   c. simultaneous application of DC potentials to control and restrict movement of ions in between each pair of surfaces, wherein the surfaces are housed in a chamber; and
   d. at least one electrically insulative shield coupled to a side plate of the chamber via a sealing member for increasing a mean-free-path between two adjacent electrodes in the chamber.

16. The device of claim 15 wherein the sealing member is an O-ring, adhesive, or sealant, and the at least one insulative shield includes electrical feedthrough housing.

17. An ion manipulation device with electrical breakdown protection comprising:
   a. a pair of surfaces including an ion inlet and an ion outlet;
   b. arrays of electrodes coupled to the surfaces to which RF potentials are applied to at least one of the surfaces in order to create a pseudopotential that inhibits charged particles from approaching the surfaces; and
   c. simultaneous application of DC potentials to control and restrict movement of ions in between each pair of surfaces, wherein the surfaces are housed in a chamber; and
   d. a first insulative shield enclosing at least part of the inlet and a second insulative shield enclosing at least a part of the outlet.

18. The device of claim 17 wherein the first and second insulative shields are made of Teflon, PEEK, or polycarbonate.

19. An ion manipulation device with electrical breakdown protection comprising:
   a. a pair of surfaces including an ion inlet and an ion outlet;
   b. arrays of electrodes coupled to the surfaces to which RF potentials are applied to at least one of the surfaces in order to create a pseudopotential that inhibits charged particles from approaching the surfaces; and
   c. simultaneous application of DC potentials to control and restrict movement of ions in between each pair of surfaces, wherein the surfaces are housed in a chamber; and
   d. a plurality of insulative shields for increasing a mean-free-path between two adjacent electrodes in the chamber, wherein the plurality of shields includes:
      i. one or more inner surface insulative shields coupled to one or more side plates of the chamber; and
      ii. one or more inlet and outlet insulative shields, wherein the inlet insulative shield encloses at least a part of the inlet, and the outlet insulative shield encloses at least a part of the outlet.

20. The device of claim 19 wherein the inner surface insulative shields are coupled to side plates via sealing member and include electrical feedthrough housing.

21. The device of claim 19 wherein the inlet and outlet insulative shields are made of Teflon, PEEK, or polycarbonate.

* * * * *